United States Patent [19]

Picha et al.

[11] Patent Number: 5,728,103
[45] Date of Patent: Mar. 17, 1998

[54] IMPLANTABLE SUBCUTANEOUS ACCESS DEVICE AND METHOD OF USING SAME

[75] Inventors: George J. Picha, Independence; Bahaman Guyuron, Hunting Valley, both of Ohio

[73] Assignee: Applied Medical Technology, Inc., Independence, Ohio

[21] Appl. No.: 702,219

[22] Filed: Aug. 23, 1996

[51] Int. Cl.⁶ .................................. A61F 11/00; A61M 5/32
[52] U.S. Cl. ................................................ 606/108; 604/174
[58] Field of Search ............................... 606/108, 170; 128/887; 604/158, 171, 174, 177, 192; D8/367, 363, 364, 356

[56] References Cited

U.S. PATENT DOCUMENTS

| | | |
|---|---|---|
| D. 358,886 | 5/1995 | Balazs . |
| 3,144,020 | 8/1964 | Zingale . |
| 3,805,770 | 4/1974 | Okada . |
| 3,815,577 | 6/1974 | Bucalo . |
| 4,321,914 | 3/1982 | Begovac et al. . |
| 4,338,937 | 7/1982 | Lerman . |
| 4,640,273 | 2/1987 | Greene et al. . |
| 4,807,593 | 2/1989 | Ito . |
| 4,834,068 | 5/1989 | Gottesman . |
| 4,850,953 | 7/1989 | Haber et al. . |
| 5,035,711 | 7/1991 | Aoki et al. . |
| 5,108,430 | 4/1992 | Ravo . |
| 5,290,249 | 3/1994 | Foster et al. ........................ 604/174 |
| 5,352,235 | 10/1994 | Koros et al. ........................ 606/170 |
| 5,356,419 | 10/1994 | Chow ................................. 606/170 |
| 5,375,588 | 12/1994 | Yoon . |
| 5,391,156 | 2/1995 | Hildwein et al. ................... 604/174 |
| 5,411,520 | 5/1995 | Nash et al. . |

Primary Examiner—Michael Buiz
Assistant Examiner—Julian W. Woo
Attorney, Agent, or Firm—Pearne, Gordon, McCoy & Granger LLP

[57] ABSTRACT

This invention relates generally to an implantable subcutaneous access device for performing an endoscopic operative procedure, and the method of using the subcutaneous access device. The subcutaneous access device is comprised of a portal sleeve, the portal sleeve preferably being angulated to provide an angulated port of entry for a surgical device through cutaneous layers of the body. A subcutaneous flange is connected to the portal sleeve in order to secure the subcutaneous access device under the cutaneous layer. An access flange which may function as a surgical mat is also connected to the portal sleeve. The method of using the subcutaneous access device consists of forming a transdermal incision, inserting the subcutaneous access device into and through the incision, and inserting and manipulating a surgical device through the port of entry to thereby perform a surgical procedure.

20 Claims, 2 Drawing Sheets

IMPLANTABLE SUBCUTANEOUS ACCESS DEVICE AND METHOD OF USING SAME

FIELD OF THE INVENTION

This invention relates generally to an improved implantable subcutaneous access device for performing endoscopic operative procedures and methods of using the subcutaneous access device wherein the subcutaneous access device can be designed to provide an angulated port of entry to interior regions of the body.

DESCRIPTION OF THE RELATED ART

A subcutaneous or percutaneous implant is an object, foreign to the body that has been placed through the skin or cutaneous layer to allow a port of entry to inner body spaces and structures. Often a port of entry is required for wires, tubes, and mechanical systems for the collection of internal information such as blood pressure, flow rate of blood, temperature, and electrocardio-signals as well as performing surgery.

The concept of providing a relatively small access port for examination and surgery is generally known as endoscopy and the use of endoscopic techniques in orthopedic, gynecological, and general surgery has had a significant effect on the traditional techniques in those specialties. Endoscopy can be used alone or in combination with more traditional "open" forms of surgery. Advantages of endoscopic assistance include direct visualization, hidden scars, and decreased morbidity.

Only recently have endoscopic techniques been introduced to plastic surgery. However, the introduction to plastic surgery, particularly to aesthetic surgery, has been very slow. Recent interest in using endoscopic techniques in forehead plasty, corrugator-procerus resection, and breast augmentation has opened up countless possibilities in these and other areas of aesthetic and reconstructive surgery. Additionally, procedures such as facial rejuvenation and abdominoplasty are being performed with endoscopic assistance.

Although plastic surgeons have been slow to incorporate endoscopic techniques into their surgical armamentarium, the application of the endoscopic method for treating the effects of aging introduces great expectation for aesthetic plastic surgery.

Subcutaneous access for chronic access applications such as chronic hemodialysis access, peritoneal dialysis access, power supply leads and fluid connection for artificial organs, charging for cardiac pacemakers, nuero-electric stimulation of nerves and/or muscles, artificial stimulation and monitoring in various brain implants is known in the art. However, a primary goal in chronic access applications is to permanently or semi-permanently secure the implantable subcutaneous device in the patient by providing holes for ingrowth of tissue or constructing the implant of porous thermoplastics or ceramics to ensure proper securement of the implant.

In addition, the related art is not generally concerned with the angle of the port of entry because most subcutaneous access applications are aimed at simply providing a port of entry to a body cavity.

Accordingly, the related art does not adequately address concerns encountered when utilizing a temporary subcutaneous access device, especially in the area of plastic and reconstructive surgery. These concerns include minimizing the impact to the surrounding tissue at the entrance site, limiting hair and foreign particle ingress into the wound, temporarily securing the implant, and providing an angulated port of entry for surgical instrumentation.

SUMMARY OF THE INVENTION

Accordingly an object of the present invention is to provide a subcutaneous access device with a temporary subcutaneous securing means to function as a means to hold the subcutaneous access device in place during the endoscopic or surgical procedure, but which permits facile removal and repositioning of the access device during a surgical procedure.

Another object of the present invention is to provide a relatively large external flange to serve as a surgical mat for endoscopic procedures, the surgical mat providing an easily identifiable entrance site for the endoscope and other associated equipment, and also serving as a shield to limit hair for foreign particle ingress into an incision.

Another object of the present invention is to provide an elastomeric lined port of entry for surgical instrumentation in order to reduce tissue damage around an incision site.

Yet another object of the present invention is to provide an angulated port of entry for endoscopic and surgical devices.

Other objections and a fuller understanding of the invention may be had by referring to the following description and claims, taken in conjunction with the accompanying drawings.

In accordance with the present invention there is provided an implantable subcutaneous access device for performing an endoscopic operative procedure in which a portal sleeve serves as a port of entry through a cutaneous layer of a body. The portal sleeve includes a subcutaneous flange adapted to be secured under the cutaneous layer, and an access flange in spaced apart relationship to the subcutaneous flange, the access flange being adapted to be positioned external to the body. The subcutaneous flange provides a surface area to prevent unintended removal of the implantable subcutaneous access device and the access flange provides a surface area which to a large degree prevents foreign particles from entering into the entry site during the endoscopic operative procedure. Generally, the portal sleeve is in the shape of a cylindrical stem, and the access and subcutaneous flanges have substantially annular shapes. In preferred embodiments, the subcutaneous access device is angulated to provide an angulated port of entry for endoscopic surgical instrumentation.

The present disclosure also provides an implantable subcutaneous access device for performing an endoscopic operative procedure wherein the surface area of the access flange is greater than the surface area of the subcutaneous flange, the access flange being in a parallel spaced apart relationship in relationship to the subcutaneous flange and preferably at an oblique angle relative to the portal sleeve.

A method of performing an endoscopic operative procedure on a portion of a body is also disclosed, and includes the steps of forming an incision extending from an external surface of the body to a subcutaneous portion of the body, placing a subcutaneous access device into and through the incision to form an elastomer lined port of entry, preferably angulated, to the subcutaneous portion of the body. The method utilizes the subcutaneous access device discussed above, comprising a portal sleeve, a subcutaneous flange connected at one end of said portal sleeve, and an access flange connected to the other end of the portal sleeve. In performing the endoscopic operative procedure, the endoscopic surgical device is inserted into and through the port of entry and manipulated subcutaneously to thereby perform the endoscopic surgical procedure. The subcutaneous flange of the subcutaneous access device preventing unintended removal of the subcutaneous access device, and the access flange providing a surgical mat which prevents foreign particles from entering into the port of entry during the endoscopic operative procedure. The method preferably utilizes the subcutaneous access device wherein the access flange is at an oblique angle relative to the portal sleeve. The method may further include any of the steps of severing, cauterizing, and suturing subcutaneous tissue, veins or arteries with the surgical instrument, and remotely viewing the surgical procedure being performed via a port of entry provided by a subcutaneous access device of the present invention.

The type of an endoscopic operative procedure which benefits from the use of an oversized external flange, an elastomer lined port of entry, and an angulated port of entry, alone or in combination, includes, but is not limited to: endoscopic brow lifting, neck lift, facelift, breast augmentation, abdominoplasty, and forehead-brow rhytidoplasty, as well as a number of other aesthetic surgical operations. In these procedures, an angulated port of entry is often preferred because the site to be sculpted is prominent in one's appearance, and angling the approach of the surgical instrumentation allows the instrument to be inserted in a more remote, less conspicuous location. Additionally, an angulated port of entry may be preferred because the incision site is penetrated may be near or over substantially skeletal or ligamentous material. In endoscopic brow lifting, elevation of the brow is achieved by inserting the subcutaneous access device through small scalp incisions, and performing the reconstructive surgery through the port of entry. This avoids the associated nerve damage of an open surgical approach, and allows for accurate excision of the muscles responsible for frowning. Additionally, endoscopic brow lifting using endoscopic techniques eliminates the use of the ear-to-ear coronal incision. The endoscopic approach accomplishes division and weakening of the corrugators, procerus, and frontalis muscles, as well as moderate elevation of the eyebrows. Excess skin is often accommodated by dissecting the scalp posteriorly toward the occiput. The elastomer lined and/or angulated port of entry is also beneficial in an endoscopic neck lift which involves inserting the access device through small incisions near the ear and undermining the skin of the neck extending from the chin to the jawline around the ear. Similarly, endoscopic facelifting avoids the need for an incision in front of the ears.

Transaxillary breast augmentation become easier using endoscopy and the subcutaneous access device of the present invention in that it utilizes the subcutaneous access device to provide a port of entry through small axillary incisions and enables precise placement of the breast augmentation implants. This results in excellent symmetry postoperatively and easy scar concealment.

Abdominoplasty is another example of a procedure usually associated with a long incision and some degree of postoperative pain and immobility. Endoscopic abdominoplasty permits not only contouring of abdominal fat through liposuction, but correction of the weakened abdominal muscle through the access port provided by the subcutaneous access device inserted into a small incision placed just above the suprapubic hairline.

DETAILED DESCRIPTION OF THE PREFERRED EMBODIMENTS

The shape of the implantable subcutaneous access device of the present invention is variable depending on the end use thereof. A typical example of the subcutaneous access device is described below in detail with reference to the accompanying drawing.

Figure 1:
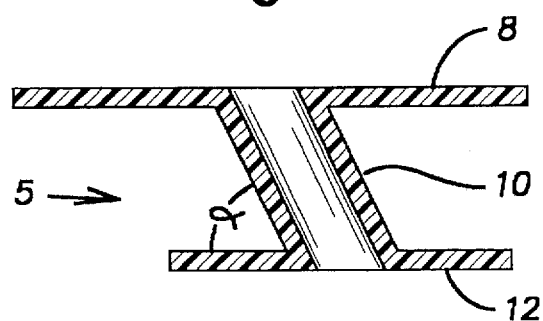
FIG. 1 is a cross sectional view of the preferred embodiment of the present invention which provides an angulated port of entry.
Figure 1A:
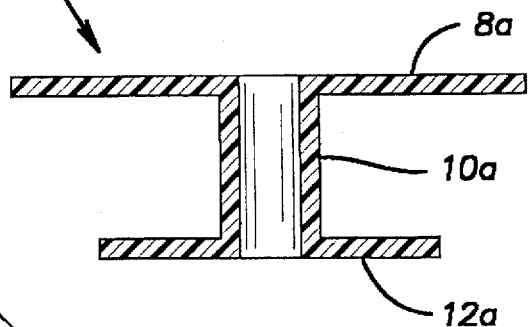
FIG. 1a is a cross sectional view of the an alternative embodiment of the present invention illustrating a perpendicular port of entry.

FIG. 1a is a cross-sectional view of an alternative embodiment of the subcutaneous access device 5a of the present invention. FIG. 1 is a cross sectional view showing an example of the preferred subcutaneous access device 5 of the present invention. The implantable subcutaneous access device 5 according to the present invention is generally fabricated from a biologically inert non-porous material. The subcutaneous access device 5, 5a may be machined, molded, cast or otherwise fabricated from full density PTFE, carbon, titanium, polycarbonate and other biologically inert materials. Preferably, the subcutaneous access device 5, 5a is composed of a bioinactive material such as silicone rubber or fluorine-contained resin. The material that comprises the subcutaneous access devices may be impregnated with biologically active material such as an antibiotic prior to implantation. The subcutaneous access device 5, 5a as shown in FIG. 1 and FIG. 1a can be manufactured in a range of dimensions and sizes. The vertical height of the subcutaneous access device 5, 5a is preferably from about 0.10 inches to about 1.25 inches.

Figure 2:
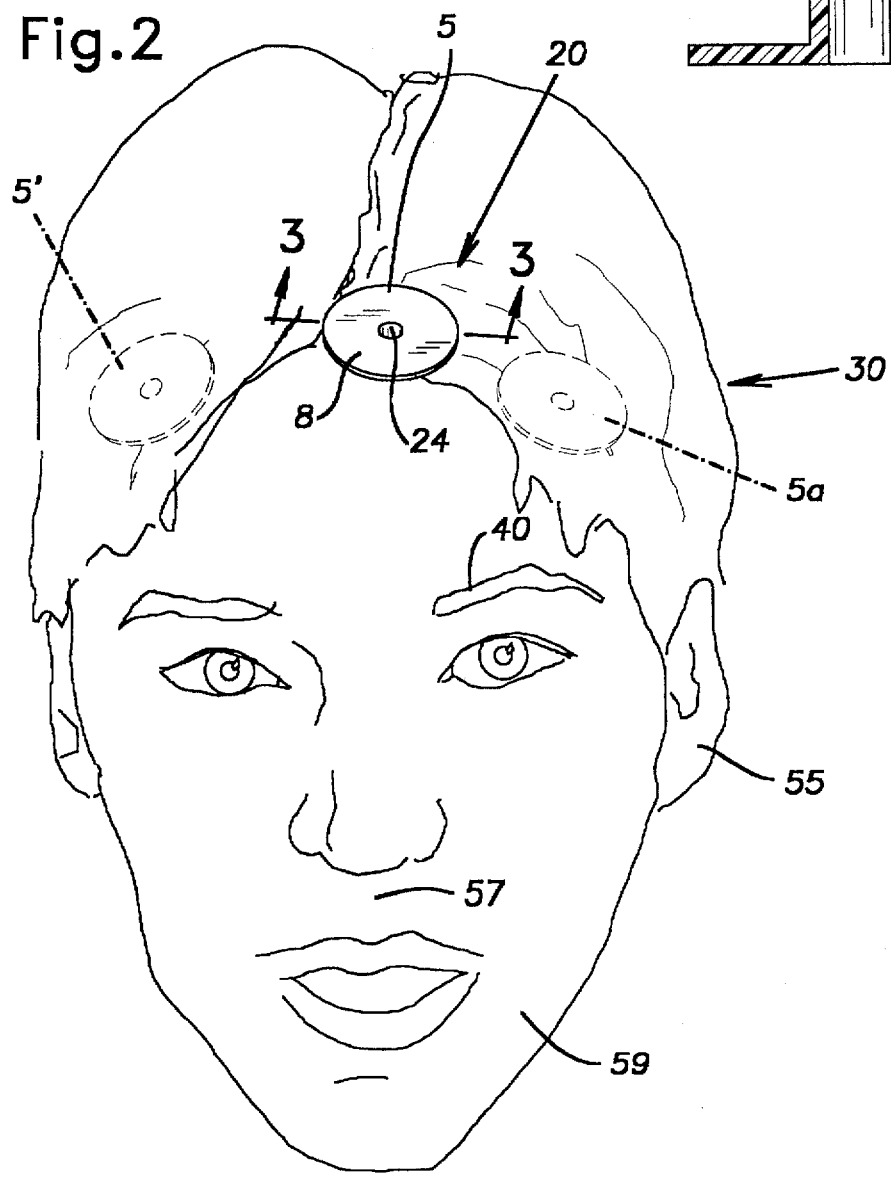
FIG. 2 illustrates a top plan view of the present invention being employed in a human subject in order to perform endoscopic brow lifting.
Figure 3:
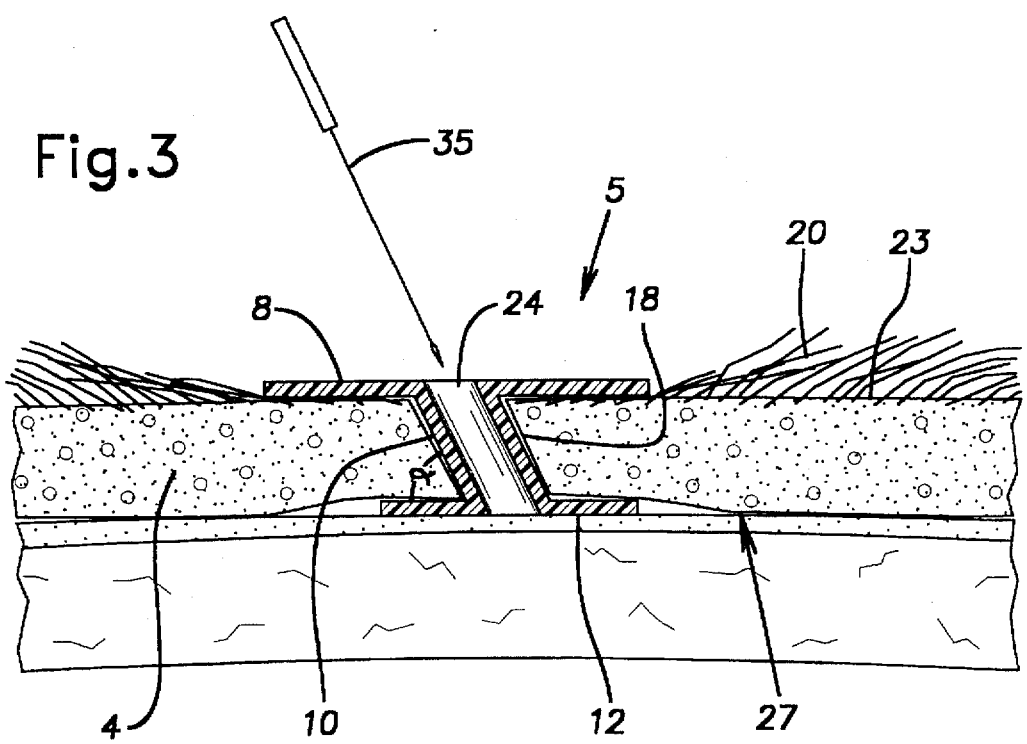
FIG. 3 is an enlarged, cross-sectional view, taken along line 3—3 of FIG. 1.
Figure 4:
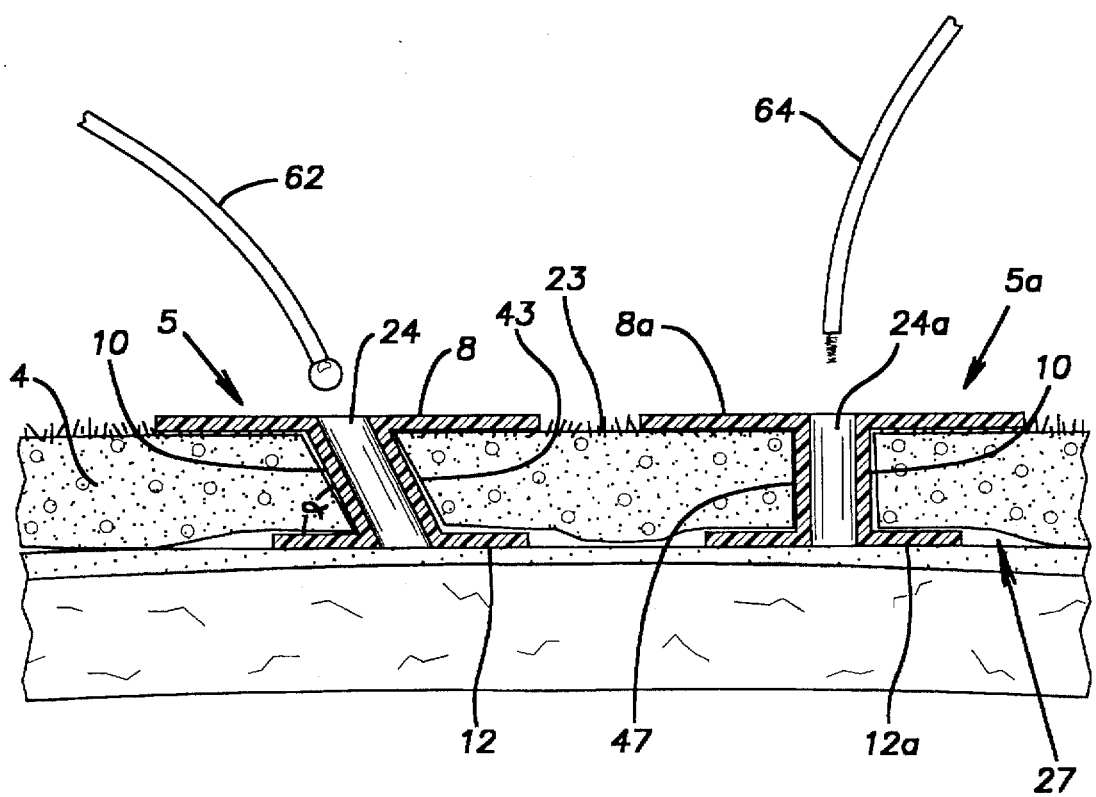
FIG. 4 is an enlarged, cross-sectional view of a subcutaneous access device providing a angulated port of entry and a subcutaneous access device providing a perpendicular port of entry being employed simultaneously.

The subcutaneous access device 5 includes an access flange 8, and a subcutaneous flange 12. Both the access flange 8, and the subcutaneous flange 12 are preferably annular in shape, and more preferable shaped as a flat disc. The access flange 8 is connected to the portal sleeve 10 at an oblique angle. As is best seen in FIGS. 2 and 3, the access flange 8 provides a surface which functions as a surgical mat, the mat making an incision site 18 easily identifiable. The access flange also holds down the hair 20 to prevent hair 20 and other foreign particles of the skin and scalp from entering into the incision site 18 during the endoscopic operative procedure. The access flange 8 receives the items to be used during the endoscopic procedure, for example, the surgical instrument 35 as shown in FIG. 3, and the video camera endoscope 62 and cauterizer 64 as shown in FIG. 4. As discussed above, the access flange 8 provides facile site recognition, and functions to prevent hair 20 and other foreign objects from entering the incision site 18.

The subcutaneous access device 5a illustrated in FIG. 1a is nearly identical to that shown in FIG. 1 except that instead of utilizing an angulated port of entry 24, a perpendicular port of entry 24a is used. The angle between the access flange 8a and the portal sleeve 10a is not oblique, rather it is 90° to provide a perpendicular port of entry 24a to be used alone or in combination with the angulated port of entry 24. FIG. 4 illustrates the simultaneous employment of subcutaneous access device 5 and 5a having angulated 24 and perpendicular 24a ports of entry. Subcutaneous access device 5a includes an access flange 8a, and a subcutaneous flange 12a. Both the access flange 8a, and the subcutaneous flange 12a are preferably annular in shape, and more preferable shaped as a flat disc.

As is best seen if FIG. 2 and FIG. 3, the access flange 8 provides a surface which functions as a surgical mat that makes an incision site 18 easily identifiable and holds down the hair 20 to prevent hair 20 and other foreign particles of the skin and scalp from entering into the incision site 18 during the endoscopic procedure. The access flange 8 receives the items to be used during the endoscopic procedure, for example, the surgical instrument 35 as shown in FIG. 3, and the video camera endoscope 62 and cauterizer 64 as shown in FIG. 4. As discussed above, the access flange 8a also of subcutaneous access device 5a provides facile site recognition, and functions to prevent hair 20 and other foreign objects from entering the incision site 47.

As shown in FIG. 3 and FIG. 4, the subcutaneous flange 12, 12a serves to support the access device 5, 5a entirely below the cutaneous layer 4. The subcutaneous flange 12, 12a providing a surface area to prevent unintended removal of the implantable subcutaneous access device 5, 5a. However, it is important to note that the diameter or surface area of the subcutaneous flange 12, 12a is preferably smaller than that of the access flange 8, 8a. The smaller diameter of the subcutaneous flange 12, 12a allows it to temporarily hold the subcutaneous access device 5 in place, while permitting facile removal and repositioning when desired. Additionally, the larger diameter access flange 8, 8a allows it to function better as a surgical mat.

The portal sleeve 10, 10a provides a port of entry 24, 24a through the cutaneous layer 4 of a portion of a body, for example the head 30. Preferably, the portal sleeve 10, 10a is in the shape of a cylindrical stem and the access flange 8, 8a and subcutaneous flange 12, 12a have substantially annular shapes. The port of entry preferably has a diameter in the range of 0.1 to about 0.25 inches and even more preferably, approximately 0.125 inches.

In the preferred embodiments, the subcutaneous flange 12 is distally located on the portal sleeve 10 of the subcutaneous access device 5, preferably in a parallel spaced apart relationship with regard to the access flange 8, and at an oblique angle α with regard to the portal sleeve 10. As defined herein, oblique angle α is defined as that angle between the subcutaneous access flange and the portal sleeve which provides an angulated or slanted port of entry 24. Accordingly oblique angle α may be any angle between 0° and 90° as shown in FIG. 1 and FIG. 2. It has been found for endoscopic purposes that α being in the range of 20°–70° is preferable, and e being in the range of 30°–60° even more preferable, with the most preferable angle α approximately 45°. Oblique angle α forming the angulated port of entry 24 provides convenient access to the subcutaneous area, and allows a surgical instrument 35 to be inserted at angle relative to the cutaneous layer 4.

The method of the present invention utilizes the preferred embodiment of the subcutaneous access device 5 having an angulated port of entry 24, alone or in combination with the alternative embodiment, subcutaneous access device 5a having the perpendicular port of entry 24a described above to perform endoscopic operative procedure on a portion of the body, i.e. reconstructive surgery on a human head or face 30 which comprises the steps of: forming an incision site 18 (FIG. 3) or a plurality of incision sites 43, 47 (FIG. 4) extending from an external surface 23 of the body to a subcutaneous portion or layer of the body 27; placing a subcutaneous access device 5, 5a into incision, the subcutaneous access device 5 providing an angulated port of entry 24 to the subcutaneous portion 27 of the body and if desired, subcutaneous access device 5a providing a perpendicular port of entry. The subcutaneous access device 5, 5a is not fixed in the incision site 18 and can be rotated about a vertical axis to allow further access to the subcutaneous portion 27. As described above, subcutaneous access device 5, 5a comprises a portal sleeve 10, 10a, a subcutaneous flange 2 connected at one end of the portal sleeve 10, 10a and an access flange 8, 8a connected to the portal sleeve 10, 10a in a spaced apart relationship relative to the subcutaneous flange 8, 8a. The method further consists of inserting an endoscopic surgical device 35 or a plurality of surgical devices such as endoscope 62 and cauterizer 64 into and through the port of entry 24, 24a to perform the desired endoscopic operative procedure. The surgical instrument 35 may be manipulated subcutaneously to thereby perform the endoscopic surgical procedure. The subcutaneous flange 12, 12a provides a surface area to prevent unintended removal of the subcutaneous access device 5, 5a, and the access flange 8, 8a provides a surface area to prevents foreign particles such as hair 20 from entering into the port of entry 24, 24a during the endoscopic operative procedure. The portal sleeve 10, 10a is preferably in the shape of a cylindrical stem and the access flange 8, 8a and the subcutaneous flange 12, 12a have substantially annular shapes. The method includes severing tissue or other subcutaneous material with the surgical instrument 35, and remotely viewing the surgical procedure being performed via the port of entry 24, 24a as well as removing the subcutaneous access device 5, 5a, and sewing closed the incision site 18 or plurality of incision sites 43, 47.

As best seen in FIG. 4, the use of endoscopic video-assisted technique in facial rejuvenation is illustrated as an example of one of the more recent advances in aesthetic plastic surgery of the face. Endoscopic video-assisted facial rejuvenation replaces the more traditional "open" technique. Video assisted endoscopy benefits from the use of the subcutaneous access device 5, alone or in combination with subcutaneous access device 5a shown for convenience in phantom in FIG. 2, and allows the physician or surgeon to be less invasive and avoid the bicoronal incision used in "open" surgery, without the necessity of skin resection. In this method, the muscles from the periorbital attachment are detached, forcing the occipital muscle to pull the forehead tissue back and thus elevating the eyebrows 40.

The angulated port of entry 24 provided when using subcutaneous access device 5 is very important to the endoscopic operative procedure known generally as facelift. As seen in FIG. 2 the angulated port of entry 24 allows for a distant incision site either at the hairline or in the region covered by hair 20, and remote operative procedures. Accordingly not only does the method of the present invention result in small scar formation, many of the scars can be hidden in the hairline or at less prominent sites.

The term facelift is preferred to rhytidoplasty because with the endoscopic facelift, facial wrinkles are not eliminated by resecting the skin or cutaneous layer 4 but by elevating facial structures, treating the facial muscles, and improving facial contour. Usually the frontal region of the face is treated subperiosteally by elevating the eyebrows 40, minimizing wrinkles, and avoiding the coronal incision. The mid-third of the face is treated subcutaneously by dissecting the skin from the SMAS, from the ear 55 to the nasolabial fold 57. If desired, the angulated subcutaneous access device 5 may be used in combination with subcutaneous access device 5a. For example, subcutaneous access device 5 is inserted through incision 43 and the second subcutaneous access device 5a may be inserted through incision 47 as seen in FIG. 4. Although FIG. 4 illustrates the use of a perpendicular port of entry 24a and a angulated port of entry, as shown in phantom in FIG. 2, subcutaneous access devices 5, 5a, and 5' may be used alone or in any desired combination. One preferred method would be to utilize subcutaneous access device 5' having an angulated port of entry 24' (not shown), the port of entry 24' being angulated towards subcutaneous access device 5. As illustrated in FIG. 4, an endoscope 62 may be inserted through incision site 43 and a cauterizer 64 through incision site 47. Blood vessels, and other subcutaneous organs and tissue may be cauterized. Plicating the SMAS and premalar fat pads to the temporal fascia treats the nasolabial fold 57 and the "jowl" region 59. In the cervical region (not shown), the platysma is treated, and with superficial liposculpture, excess fat is removed to provoke skin retraction. This permits treatment of older patients who have a more flaccid skin tone. The endoscope 62 which may include a video camera is used to help visualize the cauterizing and the suturing. The platysma can be sutured in the midline, if necessary. The cervical mental angle can be redefined with a Goretex 0 suture that passes from mastoid to mastoid.

The application of the subcutaneous access device and if use in endoscopic procedures introduces great expectation for aesthetic plastic surgery.

Hence, the true scope of the invention is only to be defined by the claims appended hereto.

What is claimed is:

1. An implantable subcutaneous access device for device for performing an endoscopic operative procedure comprising:

a portal sleeve, said portal sleeve providing a port of entry through a cutaneous layer of a body;

a subcutaneous flange connected to said portal sleeve, said subcutaneous flange being adapted to be secured under said cutaneous layer; and an access flange connected to said portal sleeve so as to be at a preformed oblique angle to the portal sleeve, said access flange being in a spaced apart relationship with said subcutaneous flange and being adapted to be located external to said body.

2. The implantable subcutaneous access device as recited in claim 1, wherein said subcutaneous flange provides a surface area to prevent unintended removal of the implantable subcutaneous access device and said access flange provides a surface area to prevent foreign particles from entering into said port of entry during the endoscopic operative procedure.

3. The implantable subcutaneous access device as recited in claim 2, wherein said portal sleeve is in the shape of a cylindrical stem.

4. The implantable subcutaneous access device as recited in claim 3, wherein the access flange and the subcutaneous flange have substantially annular shapes.

5. The implantable subcutaneous access device as recited in claim 4, wherein the surface area of the access flange is greater than the surface area of the subcutaneous flange.

6. The implantable subcutaneous access device as recited in claim 5, wherein said access flange is in a parallel spaced apart relationship with respect to said subcutaneous flange.

7. The implantable subcutaneous access device as recited in claim 6, wherein said portal sleeve further includes a proximal end and a distal end, said subcutaneous flange being connected at the distal end, and said access flange being connected at the proximal end.

8. An implantable subcutaneous access device for performing an endoscopic operative procedure comprising:

a portal sleeve providing a port of entry through a cutaneous layer of a body;

a subcutaneous flange connected to said portal sleeve so as to be at a preformed oblique angle to the portal sleeve, said subcutaneous flange providing a surface area to prevent unintended removal of the subcutaneous access device; and an access flange connected to said portal sleeve, said access flange providing a surface area to prevent foreign particles from entering into said port of entry during the endoscopic operative procedure, said access flange being in a spaced apart relationship with said subcutaneous flange.

9. The implantable subcutaneous access device as recited in claim 8, wherein said portal sleeve is in the shape of a cylindrical stem.

10. The implantable subcutaneous access device as recited in claim 9, wherein the access flange and the subcutaneous flange have substantially annular shapes.

11. The implantable subcutaneous access device as recited in claim 12, wherein said access flange is in a parallel relationship with said subcutaneous flange and at an oblique angle relative to said portal sleeve.

12. A method of performing an endoscopic operative procedure on a body comprising the steps of:

forming an incision extending from an external surface of the body to a subcutaneous portion of the body;

placing a subcutaneous access device into said incision, said subcutaneous access device providing a port of entry to the subcutaneous portion of the body, said subcutaneous access device comprising a portal sleeve, a subcutaneous flange connected at one end of said portal sleeve, and an access flange connected to said portal sleeve in a spaced apart relationship relative to said subcutaneous flange, wherein said access flanged has a substantially annular shape;

inserting an endoscopic surgical device into and through the port of entry to perform the endoscopic operative procedure; and manipulating said surgical instrument subcutaneously to thereby perform the endoscopic surgical procedure.

13. The method as recited in claim 12, wherein said subcutaneous flange provides a surface area to prevent unintended removal of the subcutaneous access device, and said access flange provides a surface area to prevents foreign particles from entering into said port of entry during the endoscopic operative procedure.

14. The method as recited in claim 13, wherein said port of entry is angulated.

15. The method as recited in claim 14, wherein said portal sleeve is in the shape of a cylindrical stem.

16. The method as recited in claim 15, wherein the subcutaneous flange has a substantially annular shape.

17. The method as recited in claim 16, wherein the surface area of the access flange is greater than the surface area of the subcutaneous flange.

18. The method as recited in claim 17, wherein said access flange is in a parallel spaced apart relationship with respect to said subcutaneous flange and at an oblique angle relative to said portal sleeve.

19. The method of as recited in claim 12, comprising the further step of:

severing tissue with said surgical instrument.

20. The method of as recited in claim 19, comprising the further step of:

remotely viewing the surgical procedure being performed via the port of entry.

* * * * *